United States Patent [19]

Valcke et al.

[11] Patent Number: 5,804,591
[45] Date of Patent: Sep. 8, 1998

[54] SYNERGISTIC COMPOSITIONS CONTAINING METCONAZOLE AND ANOTHER TRIAZOLE

[75] Inventors: Alex Raymond Albert Valcke, Wechelderzande; Mark Arthur Josepha Van der Flaas, Herselt, both of Belgium

[73] Assignee: Janssen Pharmaceutica, N.V., Beerse, Belgium

[21] Appl. No.: 765,720

[22] PCT Filed: Jun. 27, 1995

[86] PCT No.: PCT/EP95/02501

§ 371 Date: Dec. 19, 1996

§ 102(e) Date: Dec. 19, 1996

[87] PCT Pub. No.: WO96/01054

PCT Pub. Date: Jan. 18, 1996

[30] Foreign Application Priority Data

Jul. 1, 1994 [EP] European Pat. Off. ............... 94201898

[51] Int. Cl.$^6$ ..................................................... A01N 43/64
[52] U.S. Cl. ................................................................ 514/383
[58] Field of Search ................................................. 514/383

[56] References Cited

U.S. PATENT DOCUMENTS 5,599,828  2/1997  Zeun et al. ............................... 514/383

FOREIGN PATENT DOCUMENTS 0341954     11/1989  European Pat. Off. .
0 682 865 A2  5/1995  European Pat. Off. .

OTHER PUBLICATIONS

Worthing et al, "The Pesticide Manual" 9th Ed. (1991) pp. 215–216.

Primary Examiner—Allen J. Robinson
Attorney, Agent, or Firm—Ellen Ciambrone Coletti

[57] ABSTRACT

Synergistic fungicidal compositions containing a fungicidal triazole and metconazole for treating plants or the loci thereof, or for use in wood-preservation or protection of biodegradable materials. Method of treating plants comprising the administration of a fungicidal triazole and metconazole. Method of protecting wood, wood-products and biodegradable materials from fungal attack and destruction.

14 Claims, No Drawings

SYNERGISTIC COMPOSITIONS CONTAINING METCONAZOLE AND ANOTHER TRIAZOLE

CROSS-REFERENCE TO RELATED APPLICATIONS

This application claims priority from PCT/EP95/02501, filed on Jun. 27, 1995, which in turn claimed priority from EP 94.201.989.7, filed on Jul. 1, 1994.

This invention relates to synergistic compositions of metconazole and another triazole for use as fungicidal preservatives in material protection (in particular in wood), as well as for use as agrochemicals in the protection of plants, fruits and seeds. Imidazole and triazole derivatives are of particular interest as fungicidal agents and several such compounds are now widely used for this purpose. Further, combinations comprising two or more such fungicidally active compounds are known from e.g. EP-A-0,237,764, EP-A-0,393,746 and WO-95/00303.

It now has been found that compositions comprising particular ratios of metconazole and another fungicidal triazole exhibit synergistic fungicidal activity.

The present invention is concerned with compositions comprising (I) metconazole, a salt, a stereoisomer or a stereoisomeric mixture thereof, and (II) at least one other fungicidal triazole, salt, stereoisomer or stereoisomeric mixture thereof, in quantities producing a mutual synergistic effect, and a carrier.

Metconazole (I) as mentioned hereinabove is the generic name of the compound 5-[(4-chlorophenyl)methyl]-2,2-dimethyl-1-(1H-1,2,4-triazol-1-ylmethyl)cyclopentanol, which compound can be represented by the formula

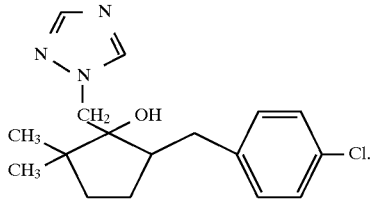

This compound, its syntheses as well as its fungicidal properties are described in EP-0,267,778, EP-0,294,222, EP-0,329,397, EP 0,357,404, EP-0,488,395, EP-0,529,976 and EP-0,576,834. Its use in biocidal compositions for the preservation of industrial materials is described in EP-0,341,954.

The other fungicidal triazole (II) mentioned hereinabove is preferably selected from:

| | |
|---|---|
| azaconazole | 1-[[2-(2,4-dichlorophenyl)-1,3-dioxolan-2-yl]methyl]-1H-1,2,4-trizole, |
| bromuconazole | 1-[4-bromo-2-(2,4-dichlorophenyl)tetrahydrofurfuryl]-1H-1,2,4-triazole, |
| cyproconazole | α-(4-chlorophenyl)-α-(1-cyclopropylethyl)-1H-1,2,4-trizole-1-ethanol, |
| difenoconazole | 1-[2-[4-(4-chlorophenoxy)-2-chlorophenyl]-4-methyl-1,3-dioxolan-2-ylmethyl]-1H-1,2,4-triazole, |
| epoxiconazole | 1-[3-(2-chlorophenyl)-2-(4-fluorophenyl)oxiran-2-ylmethyl]-1H-1,2,4-triazole |
| fenbuconazole | 4-(4-chlorophenyl)-2-phenyl-2-(1H-1,2,4-triazol-1-ylmethyl)butyronitrile, |
| hexaconazole | α-butyl-α-(2,4-dichlorophenyl)-1H-1,2,4-triazole-1-ethanol, |
| penconazole | 1-[2-(2,4-dichlorophenyl)pentyl]-1H-1,2,4-triazole, |
| propiconazole | 1-[[2-(2,4-dichlorophenyl)-4-propyl-1,3-dioxolan-2-yl]methyl]-1H-1,2,4-triazole, |
| tebuconazole | α-[2-(4-chlorophenyl)ethyl]-α-(1,1-dimethylethyl)-1H-1,2,4-triazol-1-ethanol, and |
| triticonazole | (E)-5-(4-chlorophenyl)methylene)-2,2-dimethyl-1-(1H-1,2,4-triazol-1-ylmethyl)cyclopentanol. |

The active ingredients for use in the mixtures or compositions according to the present invention may be used as stereochemical mixtures or as pure stereoisomers. In particular, metconazole may occur as 1,5-cis or 1,5-trans isomers. The 1,5-cis isomer is preferably used in the compositions of the present invention. Or use may be made of stereochemical mixtures containing predominantly (over 50%) the cis isomer.

The active ingredients (I) and (II) may be present in base or in salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid and the like; or organic acids, such as, for example, acetic, propanoic, hydroxyacetic, 2-oxopro-panoic, 2-hydroxypropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzene-sulfonic, cyclohexanesulfamic, 2-hydroxybenzoic, 4-amino-2-hydroxybenzoic and the like acids. The aforementioned salts are generally most suitable for preparing compositions for use as agrochemicals. The term salt form also comprises metal salt complexes which the active ingredients (I) or (II) may form. These metal salt complexes are generally most suitable for preparing compositions for use in material protection, in particular in wood protection. One of the ingredients may occur as a complex and the other not; or both ingredients may occur as a complex. Metal salt complexes as mentioned above consist of a complex formed between one or more active ingredients and one or more organic or inorganic metal salts. Examples of organic or inorganic metal salts comprise the halogenides, nitrates, sulfates, carbonates, hydroxides, oxides, borates, phosphates, acetates, trifluoroacetates, trichloroacetates, propionates, tartrates, sulfonates, e.g. methanesulfonates, 4-methylbenzenesulfonates, salicylates, benzoates and the like, of the metals of the second main group of the periodical system, e.g. magnesium or calcium, metals of the third or fourth main group, e.g. aluminum, tin, lead and the like metals, as well as metals of the first to the eighth transition groups of the periodical system such as, for example, chromium, manganese, iron, cobalt, nickel, copper, zinc, silver, cadmium, antimony, mercury, bismuth and the like. Preferred are the metals pertaining to the transition elements of the fourth period, in particular copper and zinc, either used alone, in combination with each other or with one or more of the metals listed above. The metal ions may be present in any of their possible valences, the most preferred metal copper being most advantageously used in its divalent form Cu(II). Suitable copper compounds are copper sulfate, acetate, hydroxide, oxide, borate, fluoride and in particular copper hydroxide carbonate $Cu(OH)_2CuCO_3$. The ratio (w/w) of the amount of copper to the total amount of triazoles (metconazole (I)+the other triazole (II)) in preferred compositions for wood-protection ranges from about 1:1 to about 20:1, and in particular is about 2:1 to about 5:1. The complexes can be mono- or polynuclear and may contain one or more parts of the active ingredients as ligands. The metal salt complexes of the active ingredients can conveniently be prepared by dissolving the metal salt in suitable solvent e.g. ethanol, and adding thereto the active ingredients. The thus obtained complexes may be isolated following art-known techniques, e.g. by filtration or evaporation, and may be further purified, e.g. by recrystallization. The term salt as used hereinabove also comprises the solvates which metconazole and the other fungicidal triazoles are able to form, e.g. hydrates, alcoholates and the like.

The synergistic mixtures according to the present invention are most useful to combat fungi or prevent the growth thereof in plants or the loci thereof; particularly in plant products, including wood; in pulpwood for paper manufacture; and also in biodegradable materials such as, for example, textiles of natural fibers, e.g. cotton, flax, hemp, wool, silk and the like; textiles of synthetic fibers, e.g. polyamide, polyacrylonitrile or polyester fibers, or of mixtures of such fibers; coatings, e.g. oil paints, dispersion paints, lacquers, lacquer films, whitewash, finishing stains and the like; glues and other such materials which are biodegradable by fungi. The synergistic mixtures of the present invention are active against a broad range of fungi. As examples of such fungi there may be named Ascomycetes (e.g. Venturia, Podosphaera, Erysiphe, Monilinia, Uncinula, Aureobasidium, Sclerophoma); Basidiomycetes (e.g. Hemileia, Rhizoctonia, Puccinia, Coniophora, Serpula, Poria, Uromyces, Gloeophyllum, Lentinus, Coriolus, Irpex); Fungi imperfecti (e.g. Botrytis, Helminthosporium, Rhynchosporium, Fusarium, Septoria, Cercospora, Alternaria, Pyricularia, Penicillium, Geotrichum.

Firstly, the synergistic mixtures according to the present invention possess advantageous curative, preventive and systemic fungicidal activity to protect plants, in particular culture plants. The present mixtures can be used to protect plants or parts of plants, e.g. fruits, blossoms, flowers, foliage, stems, roots, tubers of plants or culture plants infected, harmed or destroyed by micro-organisms, whereby later-growing parts of plants are protected against such micro-organisms. They can further be used in seed disinfection (fruits, tubers, cereal grains), to treat plant cuttings as well as to combat phytopathogenous fungi occurring in the soil. The mixtures of the present invention are particularly attractive due to their good plant tolerance and lack of environmental problems (low application rates).

As examples of the wide variety of culture plants in which the combinations of active ingredients according to the present invention can be used, there may be named for example cereals, e.g. wheat, barley, rye, oats, rice, sorghum and the like; beets, e.g. sugar beet and fodder beet; pome and stone fruits and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruits, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugar-cane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not of delimiting it thereto.

A particular mode of administering a synergistic composition containing the active ingredients (I) and (II), is the administration to the aboveground parts of plants, in particular to the leaves thereof (leaf-application). The number of applications and the administered doses are chosen in accordance with the biological and climatic conditions of life of the causative agent. The active ingredients can also be applied to the soil and get into the plants through the root system (systemic activity), in which case the locus of the plants can be sprayed with a liquid composition; or the compounds can be added to the soil in a solid formulation e.g. in the form of a granulate (soil application). The compounds (I) and (II) can be coated on seeds by drenching them either consecutively with a coating composition of each of the active ingredients individually, or alternatively by drenching the seeds with a coating composition comprising both active ingredients.

The synergistic mixtures according to the present invention are also useful as wood-preserving agents both against wood-destroying and wood-discoloring fungi. As wood which can be preserved with the synergistic compositions according to the present invention is considered, for example, wood products such as timber, lumber, railway sleepers, telephone poles, fences, wood coverings, wickerwork, windows and doors, plywood, particle board, waferboards, chipboard, joinery, bridges or wood products which are generally used in housebuilding, construction and carpentry. Synergistic compositions according to the present invention can also advantageously be applied in the cellulose and paper industry, in particular to protect pulpwood for paper manufacture from fungal attack.

Wood which is preserved from staining, discoloring and decay is meant to be protected from for example, moulding, rotting, loss of its useful mechanical properties such as breaking strength, resistance to shock and shearing strength, or decrease of its optical or other useful properties due to the occurrence of odour, staining and spot formation. These phenomena are caused by a number of micro-organisms of which the following are typical examples:

| Wood-discoloring fungi: | |
|---|---|
| 1: Ascomycetes: | Ceratocystis e.g. *Ceratocystis minor.* |
| | Aureobasidium e.g. *Aureobasidium pullulans* |
| | Sclerophoma e.g. *Sclerophoma pithyophila* |
| | Cladosporium e.g. *Cladosporium herbarum* |
| 2: Deuteromycetes: | *Fungi imperfecti* |
| | Aspergillus e.g. *Aspergillus niger* |
| | Dactylium e.g. *Dactylium fusarioides* |
| | Penicillium e.g. *P. brevicaule, P. variabile, P. funicolosum* or *P. glaucum* |
| | Scopularia e.g. *Scopularia phycomyces* |
| | Trichoderma e.g. *Tricoderma viride* or *Trichoderma lignorum.* |
| | Alternaria e.g. *Alternaria tenius*, or *Alternaria alternata* |
| 3: Zygomycetes: | Mucor e.g. *Mucor spinorus.* |
| Wood-destroying fungi | |
| 1: Soft-rot Fungi: | Chaetomium e.g. *Ch. globosum* or *Ch. alba-arenulum* |
| | Humicola e.g. *Humicola grisea* |
| | Petriella e.g. *Petriella setifera* |
| | Trichurus e.g. *Trichurus spiralis.* |
| 2: White and brown rot Fungi: | Coniophora e.g. *Coniophora puteana* |
| | Coriolus e.g. *Coriolus versicolor* |
| | Donkioporia e.g. *Donkioporia expansa* |
| | Glenospora e.g. *Glenospora graphii* |
| | Gloeophyllum e.g. *Gl. abietinum, Gl. adoratum, Gl. protactum, Gl. sepiarium* or *Gl. trabeum* |
| | Lentinus e.g. *L. cyathiformes, L. edodes, L. lepideus, L. grinus* or *L. squarrolosus* |
| | Paxillus e.g. *Paxillus panuoides* |
| | Pleurotus e.g. *Pleurotis ostreatus* |
| | Poria e.g. *P. monticola, P. placenta, P. vaillantii* or *P. vaporaria* |
| | Serpula (Merulius) e.g. *Serpula himantoides* or *Serpula lacrymans* |
| | Stereum e.g. *Stereum hirsutum* |
| | Trychophyton e.g. *Trychophyton mentagrophytes* |
| | Tyromyces e.g. *Tyromyces palustris.* |

In order to protect wood from decay it is treated with synergistic compositions according to the present invention. Such treatment is applied by several different procedures such as, for example, by treating the wood in closed pressure or vacuum systems, in thermal or dip systems and the like, or by a wide variety of surface treatments, e.g. by brushing, dipping, spraying or soaking the wood with a formulation containing the wood-preserving agents metconazole and a fungicidal triazole.

The amount of each of the active ingredients metconazole (I) and the fungicidal triazole (II) in the compositions according to the present invention is such that a mutual synergistic fungicidal effect is obtained upon application. In particular, it is contemplated that in the compositions to be used directly, the concentration of metconazole taken as base equivalent, may range from 10 to 15000 ppm, in particular from 50 to 12000 ppm or from 50 to 6000 ppm, more in particular from 100 to 3000 ppm; and the concentration of the other azole taken as base equivalent is contemplated to range from 10 to 15000 ppm, in particular from 50 to 10000 ppm or from 100 to 8000 ppm, more in particular from 200 to 6000 ppm. In many instances said compositions to be used directly can be obtained from concentrates upon dilution with aqueous or organic media, such concentrates also being intended to be covered by the term composition as used in the definitions of the present invention. The content of the active ingredients in the above-indicated compositions is from 0.01 to 95%, preferably from 0.1 to 50% more preferably from 0.1 to 20% and in particular from 0.2 to 15% by weight. The compositions according to the invention are preferably used in the form of solutions or emulsions.

The ratio between the active ingredients of formula (I) and (II) in said synergistic compositions may vary within relatively broad ranges and will be dependent on the nature of the active ingredient (II). However, said ratio will be such that a mutual synergistic fungicidal effect is obtained. Particularly, it is contemplated that the weight ratio between the active ingredients (I) and (II) (metconazole: the other triazole) may be situated between 50:1 and 1:50, more particularly between 20:1 and 1:20. Preferably said ratio is between 10:1 and 1:10, more preferably between 5:1 and 1:5.

The active ingredients of formula (I) and (II) are used in unmodified form or together with adjuvants conventionally employed in the art of formulation. The formulations, i.e. the compositions, preparations or mixtures containing the active ingredients and, where appropriate, a solid or liquid adjuvant, are prepared following art-known procedures, e.g. by homogeneously mixing and/or grinding the active ingredients with extenders, e.g. solvents, solid carriers and, where appropriate, surface-active compounds (surfactants), to emulsifiable concentrates, directly sprayable or dilutable solutions, dilute emulsions, wettable powders, soluble powders, dusts, granulates, and also encapsulations in e.g. polymer substances. Both the nature of the compositions and the methods of application such as spraying, atomizing, dusting, scattering or pouring, brushing, dipping, soaking or impregnating, should be chosen in accordance with the intended objectives and the prevailing circumstances. It is evident that in general different compositions with different characteristics will be required for use in plant protection on the one hand, and for use in material protection on the other. Carriers and adjuvants equally useful in both types of compositions are described first.

Appropriate carriers and adjuvants for use in the compositions of the present invention may be solid or liquid and correspond to suitable substances known in the art for preparing formulations for treating plants or the loci thereof, or for treating plant products, in particular for treating wood, such as, for example, natural or regenerated mineral substances, solvents, dispersants, surfactants, wetting agents, adhesives, thickeners, binders, fertilizers, anti-freeze agents, repellents, colour additives, corrosion inhibitors, water-repelling agents, siccatives, UV-stabilizers and other active ingredients.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water, or a mixture of said solvents.

Suitable surface-active compounds to be used in the compositions of the present invention are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylaryl-sulfonates. The fatty sulfonates or sulfates are usually in the form of alkali metal salts, earth alkaline metal salts or unsubstituted or substituted ammonium salts and contain an alkyl radical having from 8 to 22 carbon atoms said alkyl also comprising radicals derived from acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenol polyethoxy-ethanols, castor oil polyglycol ethers, polypropylenelpolyethylene oxide adducts, tributylphenoxy-polyethoxyethanol, polyethylene glycol and octylphenoxypolyethoxyethanol. Fatty acid esters of polyethylene sorbitan, such as polyoxyethylene sorbitan trioleate, are also suitable non-ionic surfactants. They are of particular utility in compositions for material, in particular wood, protection.

Cationic surfactants are preferably quaternary ammonium salts wherein at least one N-substituent is a $C_8$–$C_{22}$alkyl radical and the further substituents are unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide. They are particularly useful in compositions for agrochemical purposes.

The surfactants customarily employed in the art of formulation are described e.g. in the following publications: "McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

The following paragraphs in particular relate to compositions for use in plant protection. In general such compositions are designed so as to be innocuous to culture plants, to be easily and safely applicable, to have good bioavailability to the host plants and to remain (persist) only temporarily in the environment.

Particularly advantageous additives useful to improve the application and reduce the dose of the active ingredients, are the natural (animal or plant) or synthetic phospholipids of the cephalin or lecithin type such as, for example, phosphatidyl-ethanolamine, phosphatidyl serine, phosphatidylglycerine, lysolecithin, or cardiolipin. Such phospholipids may be obtained from animal or plant cells, in particular from brain-, heart- or liver tissue, egg yolks or soy beans. Appropriate such phospholipids are for instance, phosphatidylcholine mixtures. Synthetic phospholipids are for instance, dioctanylphosphatidylcholine and dipalmitoylphosphatidylcholine.

In case of liquid formulations, and particularly of aqueous or alcoholic formulations, it is recommendable to add an appropriate surfactant, either from the anionic, cationic, nonionic or amphoteric type. In particular said surfactants will be of the cationic type and more in particular said surfactant is a quaternary ammonium salt or a mixture of quaternary ammonium salts. Such quaternary ammonium surfactants comprise, for example, ammonium salts having four hydrocarbon radicals which may optionally be substituted with halo, phenyl, substituted phenyl or hydroxy; said hydrocarbon radicals in particular being alkyl or alkenyl radicals; they may also be derived from fatty acids or alcohols, e.g. cetyl, lauryl, palmityl, myristyl, oleyl and the like or from the hydrosylates form coconut oil, tallow oil, soy bean oil, or the hydrogenated forms thereof, and the like.

Examples of such quaternary ammnonium salts are of the trimethyl alkyl ammonium halide type, e.g. trimethyl decyl ammonium chloride, trimethyl dodecylammonium chloride, trimethyl tallow ammonium chloride, trimethyl oleyl ammonium chloride; or of the dimethyl alkyl benzyl ammonium type, e.g. dimethyl decyl benzyl ammonium chloride, dimethyldodecyl benzyl ammonium chloride, dimethyl hexadecylbenzyl ammonium chloride (commonly designated as "cetalkonium chloride"), dimethyl octadecyl benzyl ammonium chloride, dimethyl coco benzyl ammonium chloride, dimethyl tallow benzyl ammonium chloride; and particularly the dimethyl $C_{8-18}$alkyl benzyl ammonium chloride mixture which is commonly known as "benzalkonium chloride"; dimethyl dialkyl ammonium halides, e.g. dimethyl dioctyl ammonium chloride, dimethyl didecyl ammonium chloride, dimethyl didodecyl ammonium chloride, dimethyl dicoco ammonium chloride, dimethyl ditallow ammonium chloride, dimethyl octyl decyl ammonium chloride, dimethyl dodecyl octyl ammonium chloride, dimethyl dihydrogenated tallow ammonium chloride.

As used in the foregoing enumeration of quaternary ammonium salts, the terms "coco", "tallow" and "hydrogenated tallow" designate those hydrocarbon radicals derived from the hydrosylates of coconut oil, tallow oil or hydrogenated tallow oil. The weight ratio between said quaternary ammonium surfactants and the active ingredient (I) is situated between 1:1 and 10:1. Excellent results are obtained when said ratio is about 5:1.

The following paragraphs in particular relate to compositions for use in wood protection. In general such compositions are designed so as to penetrate well in to wood, to persist there for a long time, and to be industrially applicable.

A biocidally active quaternary ammonium compound or tertiary amine salt can advantageously be used in the formulation of emulsions of triazole compounds in aqueous solutions of metal salts. Micro-emulsions may thus be formed which have particular utility in wood preservation. Additional advantages related to these adjuvants comprise their solubilizing effect on the triazole compounds, their contributory biocidal effect and their ability to promote penetration of the formulation into wood.

Binders are meant to comprise binding drying oils (e.g. linseed oil) and resins that are water-dilutable or dilutable, dispersable or emulsifiable in organic solvents, e.g. acryl, vinyl, polyester, polyurethane, alkyd, phenolic, hydrocarbon and silicon resins. Mixtures of an alkyd resin with a drying oil are advantageously used as a binding material. Part of the binding material may further be substituted with one or more fixing agents or one or more plasticizers. These adjuvants delay or prevent evaporation of the active ingredients as well precipitation or crystallisation thereof. About 0.01% to about 30% of the binding material may thus be replaced. Suitable plasticizers are phthalic acid esters, e.g. the dibutyl, dioctyl and benzylbutyl phthalate esters; phosphoric acid esters, e.g. tributylphosphate; fatty acid esters, e.g. di(2-ethylhexyl) adipate, butylstearate, amylstearate, butyloleate; glycerolethers; glycolethers; glycerolesters; and p-toluenesulfonic acid esters. Suitable fixing agents are polyvinylalkyl ethers, e.g. polyvinylmethyl ethers, or ketones, e.g. benzophenone or ethylenebenzophenone.

In view of their solubility in organic solvents the active ingredients are well suited for application in non-aqueous media, which is of interest in wood-preservation. The wood or wood products to be protected can easily be impregnated with such solutions. As organic solvents there may be used aliphatic and aromatic hydrocarbons, their chlorinated derivatives, acid amides, mineral oils, alcohols, ethers, glycolethers, such as, for example, methylene chloride, propylene glycol, methoxyethanol, ethoxyethanol, N,N-dimethylform-amide and the like or mixtures of such solvents, to which there may be added dispersants or emulsifiers such as sulfated ricinus oil, fatty alcohol sulfates and other additives.

Particularly attractive formulations comprise water-dilutable wood-preservative liquids containing an appropriate amount of a suitable solvent, a suitable solubilizer and both the active ingredients. Preferably there is used 10–80% of a solvent, 20–80% of a solubilizer and from 0.01 to 10% of the active ingredients (1) and (II).

Preferred solubilizers to be used in the said water-dilutable wood-preservative liquids are selected from:
i) addition products of 1 to 60 moles of ethylene oxide with 1 mole of a phenol which is further substituted with at least one $C_{1-15}$ alkyl group; and
ii) addition products of 1 to 60 moles of ethylene oxide with 1 mole of ricinus oil.

The most preferred solubilizers are selected from:
i) addition products of 1 to 60 moles of ethylene oxide with 1 mole of nonylphenol or octylphenol; and
ii) addition products of 1 to 60 moles of ethylene oxide with 1 mole of ricinus oil.

Said suitable solvent should fulfil the requirements of sufficiently solubilizing the active ingredients and, when combined with the solubilizer, of being homogeneously miscible with a predominantly aqueous medium. Preferred solvents are 2-butoxyethanol, butyl 2-hydroxyacetic acid ester and propyleneglycol monomethylether.

Preferred water-dilutable compositions for use in wood protection comprise (I) metconazole, the other fungicidal triazole (II), a copper compound, suitable solvents and/or solubility enhancers and optionally other adjuvants. Suitable solvents are e.g. alcohols (ethanol, iso-propanol), glycols (ethylene and propylene glycol), glycolethers (ethylene glycol monomethyl and monoethyl ether), dimethylformarnide, n-methylpyrrolidone, which yield homogeneous concentrates. As solubilizers there may be employed carboxylic acids, or the amine, alkali metal or copper salt forms corresponding thereto, so that the amount of the organic solvent used in the homogenous concentrates can be kept to a minimum. Examples of such acids are propionic, hexanoic, heptanoic, 2-ethylhexanoic, iso-octanoic, sebacic, cyclohexanoic, benzoic, 3-hydroxybenzoic and 4-hydroxybenzoic acid. To improve further the industrial applicability of such water-dilutable, homogenous compositions comprising a carboxylic acid as solubilizer, advantageous use may be made of polyethyleneimines (PEI, Polymin) derived from ethyleneimine (aziridine) and having the formula $(C_2H_5N)_n$. The degree of polymerization 'n' should be larger than 10 and preferably ranges from about 50 to about 1000, and in particular is about 150. The use of alkanolamines, in particular monoethanolamine, but also di- and triethanolamine, as complexing agents for the copper compound employed may be of particular benefit. Typically there may be used about 4 molar equivalents of alkanolamine per mole of copper. Further useful additives are, for example, boron derivatives, e.g. boric acid, its salts and esters, and fluorides, e.g. potassium fluoride.

Water-dilutable homogenous concentrates in particular comprise by weight:

2.5 to 45%, in particular 10 to 20% copper compound,
5 to 50%, in particular 20 to 40% alkanolamine,
0.25 to 15%, in particular 1 to 10% triazoles (I+II),
0.5 to 30%, in particular 5 to 15% surfactant(s),
0 to 40% other fungicidal compound(s),
0 to 40% organic solvent(s),
0 to 40% carboxylic acid(s), and
0 to 40% polymin.

Said water-dilutable wood-preserving liquids have the advantage that almost instantaneously homogeneous or quasi homogeneous solutions are formed by mixing these liquids with predominantly aqueous media. These solutions have an extremely high physical stability, not only at ambient temperature, i.e. at temperatures comprised between 15° C. and 35° C., but also at decreased temperatures. Thus, the physical stability of said solutions does not deteriorate after several freeze-thaw cycles. Said homogeneous solutions further unite the advantages of moistening the wood-surface well and penetrating the wood to a high degree, resulting in a high uptake of the solution and its active ingredients by the wood, and, consequently, obtaining the desired preservation of the treated wood. Additionally, due to a more uniform uptake of the aqueous solution the wood-preserving liquids and the resulting aqueous solutions are particularly useful in treatment techniques which require the possibility of a continuous process, such as, for example, impregnation or dip techniques. In addition, the solutions formed with the wood-preserving liquids unite in themselves the hereinabove mentioned advantages with those which are characteristic of predominantly aqueous media, such as, for example, a relatively high flashpoint and reduced toxicity, resulting in advantageous influence on the environment and the health and safety of the applicator, lack of irritation and the like benefits.

In the wood-preserving solutions which are used to be contacted with the wood, said solutions either being a composition as described hereinabove or prepared therefrom upon dilution with a suitable solvent, the concentration of metconazole may vary between 100 and 10000 ppm, in particular between 200 and 5000 ppm and preferably between 500 and 1000 ppm; the concentration of the compound of formula (II) may vary between 100 and 15000 ppm, in particular between 300 and 7500 ppm and preferably between 750 and 1500 ppm.

In said wood-preserving solutions, the ratio between the active ingredients (I) and (II) (metconazole/a fungicidal triazole) will be such that a synergistic fungicidal effect is obtained with both active ingredients. Particularly, the weight ratio between (I) and (II) may range from 20:1 to 1:20, more particularly from 10:1 to 1:10 and preferably will range from about 5:1 to 1:5. When the fungical triazole (II) is propiconazole, the weight ratio between (I) and (II) preferably ranges from 2:1 to 1:4, more particularly from 1:1 to 1:3 and preferably will be about 1:2.

Apart from both the aforementioned active ingredients of formula (I) and (II), the compositions according to the present invention may further contain other active ingredients, e.g. other microbiocides, in particular insecticides, and also bactericides, acaricides, nematicides, herbicides, plant growth regulators, fertilizers or further fungicides. As antimicrobial agents, which may be used in combination with the active substances there may be considered products of the following classes: phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol, tribromophenol, tetrachlorophenol, 3-methyl-4-chlorophenol; chlorinated hydroxydiphenylethers such as, for example, 2-hydroxy-3,2'4'-trichlorodiphenylether; phenylphenol (o-, m-, p-), 4-chloro-2-phenylphenol, 4-chloro-2-benzylphenol, dichlorophene, hexachlorophene; aldehydes such as formaldehyde, glutaraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; diiodomethyl-p-tolylsulfone, 3-iodo-2-propynyl-alkohol, 4-chlorophenyl-3-iodopropargyl-formal, 3-bromo-2,3-diiodo-2-propenylethylcarb-Rat, 2,3,3-triiodoallylalkohol, 3-bromo-2,3-diiodo-2-propenylalkohol, 3-iodo2-propynyl-n-butylcarbamate, 3-iodo-2-propynyl-n-hexylcarbamate, 3-iodo-2-propynyl-cyclohexylcarbamate, 3-iodo2-propynyl-phenyl-carbamate; mono-, di- and polyamines such as dodecylamine or 1,10-di(n-heptyl)-1, 10-diaminodecane; sulfonium- and phosphonium compounds; mercapto compounds as well as their alkali, earth alkaline and heavy metal salts such as 2-mercaptopyridine-N-oxide and its sodium, iron, manganese and zinc salt, 3-mercaptopyridazin-2-oxide, 2-mercaptoquinoxaline-1-oxide, 2-mercaptoquinoxaline-di-N-oxide, as well as the symmetrical disulfides of said mercapto compounds; ureas such as tribromo- or trichlorocarbanilide, dichlorotrifluoromethyl-diphenylurea; tribromosalicylanilide; 2-bromo-2-nitro-1,3-dihydroxypropane (bronopol); dichlorobenzoxazolone; chlorohexidine; sulfenamides e.g. dichlofluanid, tolylfluanid, folpet, fluorfolpet; benzimidazoles e.g. carbendazim, benomyl, fuberidazole, thiabendazole; thiocyanates e.g. thiocyanatomethylthiobenzothiazole, methylenebisthiocyanate; quaternary ammonium compounds e.g. benzyldimethyltetradecyl ammonium chloride, benzyldimethyldodecyl ammonium chloride, didecyldimethyl ammonium chloride; morpholine derivates e.g. tridemorph, fenpropimorph, falimorph; azoles e.g. triadimefon, triadimenol, bitertanol, prochloraz; 2-(1-chlorocyclopropyl)-1-(2-chlorophenyl)-3-(1H-1,2,4-triazol-1-yl)-propan-2-ol; isothiazolinones e.g. N-methylisothiazolin-3-one, 5-chloro-N-methyl-isothiazolin-3-one, 4,5-dichloro-N-octylisothiazolin-3-one, N-octyl-isothiazolin-3-one; benzisothiazolinone, cyclopenteneisothiazolinone; tetrachloro-4-methylsulfonylpyridine; metal salts e.g. tin, copper, zink naphthenate, octoate, 2-ethylhexanoate, oleate, phosphate, benzoate; oxides e.g. tributyltin oxide, $Cu_2O$, CuO, ZnO; dialkyldithiocarbamate e.g. Na- and Zn-salts of dialkyldithiocarbamates, tetramethylthiuramdisulfide; nitriles e.g. 2,4,5,6-tetrachloroisophthalodinitrile; benzothiazole e.g. 2-mercaptobenzothiazole; quinolines e.g. 8-hydroxyquinoline and its Cu-salts; boron compounds e.g. boric acid, boric acid esters, borax; formaldehyde and formaldehyde releasing compounds e.g. benzylalkohol mono (poly)hemiformal, oxazolidine, hexahydro-S-triazine, N-methylol-chloracetamide, paraformaldehyde; tris-N-(cyclohexyldiazeniumdioxy)-aluminium, N-cyclohexyldiazeniumdioxy)-tributyltin bisN-(cyclohexyldiazeniumdioxy)-copper.

As insecticidal agents which may be used in the combination according to the present invention the following classes of products may be considered: insecticides having a natural origin, e.g., nicotine, rotenone, pyrethrum and the like; chlorinated hydrocarbons, e.g., lindane, chlordane, endosulfan and the like; organic phosphor compounds, e.g. azinphos-ethyl, azinphos-methyl, 1-(4-chlorphenyl)-4(0-ethyl, S-propyl)phosphoryl-oxypyrazole, chlorpyrifos, coumaphos, demeton, demeton-S-methyl, diazinon, dichlorvos, dimethoate, ethoprophos, etrimfos, fenitrothion, fenthion, heptenophos, parathion, parathionmethyl, phosalone, phoxim, pirimiphos-ethyl, pirimiphos-methyl, profenofos, prothiofos, sulfprofos, triazophos, trichlorphon; carbamates, e.g., aldicarb, bendiocarb, carbaryl, carbofuran, carbosulfan, cloethocarb, 2-(1-methylpropyl) phenylmethylcarbamate, butocarboxime, butoxycarboxime, fenoxycarb, isoprocarb, methomyl, methiocarb, oxamyl, pirimicarb, promecarb, propoxur and thiodicarb;; biological insecticides, e.g., products originating from *Bacillus thuringiensis*; synthetic pyrethroids, e.g., allethrin, alphamethrin, bioresmethrin, bifenthrin, cycloprothrin, cyfluthrin, cyhalothrin, cypermethrin, decamethrin, deltamethrin, fenpropathrin, fenfluthrin, fenvalerate, flucythrinate, flumethrin, fluvalinate, halothrin, permethrin, resmethrin and tralomethrin, alpha-cyano-3-phenyl-2-methylbenzyl-2-2-dimethyl-3-(2-chloro-2-trifluoromethylvinyl)cyclopropancarboxylate; organosilicon compounds such as dimethylphenylsilylmethyl-3-phenoxybenzylethers e.g. dimethyl(4-ethoxyphenyl) silylmethyl-3-phenoxybenzylether; or dimethylphenylsilylmethyl-2-phenoxy-6-pyridylmethylethers e.g. dimethyl(9-ethoxy-phenyl) silylmethyl-2-phenoxy-6-pyridylmethylether or [(phenyl)-3-(3-phenoxyphenyl)propyl](dimethyl)silanes e.g. (4-ethoxyphenyl)[3-(4-fluoro-3-phenoxyphenyl)propyl] dimethylsilane, silafluofen; nitroimines and nitromethylenes e.g. 1 (6-chloro-3-pyridinylmethyl)-4,5-dihydro-N-nitro-1H-imidazol-2-amine (imidacloprid); benzoylureas e.g. lufenuron, hexaflumuron, flufenoxuron.

Particularly interesting active ingredients for combination with the present metconazole/triazole synergistic mixtures are: dichlofluanid, tolylfluanid, benzyldimethyldodecyl ammonium chloride, didecyldimethyl ammonium chloride, 3-bromo-2,3-diiodo-2-propenylalcohol, 3-iodo-2-propinyl-n-butylcarbamate, o-phenylphenol, m-phenylphenol, p-phenylphenol, 3-methyl-4-chlorophenol, thiocyanatomethylthiobenzothiazole, N-methyl-isothiazolin-3-one, 5-chloro-N-methylisothiazolin-3-one, 4,5-dichloro-N-octylisothiazolin-3-one, N-octyl-isothiazolin-3-one, benzylalkoholmono(poly)hemiformal, N-methylolchloracetamide, phoxim, cyfluthrin, permethrin, cypermethrin, deltamethrin, imidacloprid, silafluofen, lufenuron, bifenthrin, fenoxycarb, hexaflumuron, flufenoxuron.

Susceptible material (in particular wood) destroying insects are, for example:

| Beetles | Hymenoptera: |
|---|---|
| Anobium punctatum | Sirex juvencus |
| Apate monachus | Urocerus augur |
| Bostrychus capucinus | Urocerus gigas |
| Chlorophores pilosus | Urocerus gigas taignus. |
| Dendrobium pertinex | Termites: |
| Dinoderus minutus | Coptotermes formosanus |
| Ernobius mollis | Cryptotermes brevis |
| Heterobostrychus brunneus | Heterotermes indicola |
| Hylotrupes bajulus | Kalotermes flavicollis |
| Lyctus africanus | Mastotermes darwiniensis |
| Lyctus brunneus | Reticulitermes flavipes |
| Lyctus linearis | Reticulitermes lucifugus |
| Lyctus planicollis | Reticulitermes santonensis |
| Lyctus pubescens | Zootermopsis nevadensis. |
| Minthea rugicollis | |
| Priobium carpini | |
| Ptilinus pecticornis | |
| Sinoxylon spp. | |
| Trogoxylon aequale | |
| Tryptodendron spp. | |
| Xestobium rufovillosum | |
| Xyleborus spp. | |

The synergistic mixtures or compositions to be used directly may also be obtained from separate compositions containing the active ingredients or from the technical active ingredients themselves, by mixing and/or diluting with aqueous or organic media and/or optionally further adding adjuvants such as those described hereinabove. Said separate compositions generally are such as described hereinbefore for compositions containing both active ingredients. Of particular interest to some users may be preparation of custom-made formulations from both active ingredients in unmodified, technical form, thus allowing maximal flexibility in the application of the present synergistic mixtures of metconazole and a fungicidal triazole.

The present invention also concerns a method of combating fungi comprising treating plants or the loci thereof, or treating plant products such as wood; or pulpwood for paper manufacture, or treating biodegradable materials simultaneously, separately or sequentially with an effective amount of a synergistic, fungicidal composition as described hereinabove.

The present invention also concerns a method of preserving wood, wood products and biodegradable materials from deterioration by fungi. This method comprises the application to or incorporation in said wood or wood products or in or to said biodegradable materials, of a synergistic mixture or composition as defined hereinabove.

Metconazole (I) and the fungicidal triazole (II) can be applied to plants or to the loci thereof or to plant products, e.g. wood, or to biodegradable materials such as textiles, simultaneously, or can also be applied consecutively within a time period selected so that both active ingredients are allowed to act synergistically as antifungals, e.g. within 24 hours. In such applications, the active ingredients are used optionally together with adjuvants conventionally employed in the art of formulation such as carriers, surfactants or other useful additives. Therefore, the present invention also concerns products containing (I) metconazole, a salt, a stereoisomer or a stereoisomeric mixture thereof, and (II) a fungicidal triazole, a salt, a stereoisomer or a stereoisomeric mixture thereof, as a combination for simultaneous, separate or sequential use in fungicidal applications. Such products may consists of a package comprising containers with both active ingredients, preferably in formulated form. Such formulated forms in general have the same composition as described for the formulations containing both active ingredients.

The following examples are intended to illustrate the scope of the present invention in all its aspects. Unless otherwise stated all parts therein are by weight.

EXAMPLES

Throughout all examples percentages are by weight.
A) COMPOSITION EXAMPLES (Plant protection)

| Example 1: Wettable powders | a) | b) | c) |
|---|---|---|---|
| metconazole | 10% | 25% | 0.25% |
| a fungicidal triazole (azaconazole) | 10% | 25% | 0.25% |
| sodium lignosulfonate | 5% | 5% | 5% |

| Example 1: Wettable powders | a) | b) | c) |
|---|---|---|---|
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredients were thoroughly mixed with the adjuvants and the mixture was thoroughly ground in a suitable mill, affording wettable powders which could be diluted with water to give suspensions of the desired concentration.

| Example 2: Emulsifiable concentrates | a) | b) | c) | d) |
|---|---|---|---|---|
| metconazole | 5% | 0.5% | 7% | 9% |
| a fungicidal triazole (bromuconazole) | 5% | 0.5% | 3% | 1% |
| octylphenol polyethylene glycol ether (4–5 moles of ethylene oxide) | 3% | 3% | 3% | 3% |
| calcium dodecylbenzenesulfonate | 3% | 3% | 3% | 3% |
| castor oil polyglycol ether (36 moles of ethylene oxide) | 4% | 4% | 4% | 4% |
| cyclohexanone | 30% | 10% | 30% | 30% |
| dimethylbenzene mixture | 50% | 79% | 50% | 50% |

| | e) | f) | g) | h) |
|---|---|---|---|---|
| metconazole | 5% | 2.5% | 4% | 9% |
| a fungicidal triazole (tebuconazole) | 5% | 2.5% | 1% | 1% |
| calcium dodecylbenzenesulfonate | 5% | 8% | 8% | 5% |
| castor oil polyethylene glycol ether (36 moles of ethylene oxide) | 5% | — | — | 5% |
| tributylphenol polyethylene glycol ether (30 moles of ethylene oxide) | — | 12% | 12% | — |
| cyclohexanone | — | 15% | 15% | — |
| dimethylbenzene mixture | 80% | 60% | 60% | 80% |

Emulsions of any required concentration could be obtained from these concentrates by dilution with water.

| Example 3: Dusts | a) | b) | c) | d) |
|---|---|---|---|---|
| metconazole | 0.05% | 0.5% | 0.075% | 0.095% |
| a fungicidal triazole (cyproconazole) | 0.05% | 0.5% | 0.025% | 0.005% |
| talcum | 99.9% | — | 99.9% | 99.9% |
| kaolin | — | 99% | — | — |

Usable dusts were obtained by mixing the active ingredients with the carriers, and grinding the mixture in a suitable mill.

| Example 4: Extruder granulates | a) | b) | c) | d) |
|---|---|---|---|---|
| metconazole | 5% | 0.5% | 9.5% | 0.9% |
| a fungicidal triazole (difenoconazole) | 5% | 0.5% | 0.5% | 0.1% |
| sodium lignosulfate | 2% | 2% | 2% | 2% |
| carboxymethylcellulose | 1% | 1% | 1% | 1% |
| kaolin | 87% | 96% | 87% | 96% |

The active ingredients were mixed and ground with the adjuvants, and the mixture was subsequently moistened with water. The mixture was extruded and dried in a stream of air.

| | e) | f) | g) | h) |
|---|---|---|---|---|
| metconazole | 2.5% | 5% | 4.5% | 8% |
| a fungicidal triazole (epoxiconazole) | 2.5% | 5% | 0.5% | 2% |
| kaolin | 94% | — | 94% | — |
| highly dispersed silicic acid | 1% | — | 1% | — |
| attapulgite | — | 90% | — | 90% |

The active ingredients were dissolved in dichloromethane, the solution was sprayed onto the carrier, and the solvent was subsequently evaporated off in vacuo.

| Example 5: Coated granulates | a) | b) | c) |
|---|---|---|---|
| metconazole | 1.5% | 4% | 9% |
| a fungicidal triazole (triticonazole) | 1.5% | 1% | 1% |
| polyethylene glycol (mol. wt. 200) | 2% | 2% | 2% |
| kaolin | 95% | 93% | 88% |

The active ingredients were uniformly applied, in a mixer, to the kaolin moistened with polyethylene glycol. Non-dusty coated granulates were obtained in this manner.

| Example 6: Suspension concentrates | a) | b) | c) | d) |
|---|---|---|---|---|
| metconazole | 20% | 2.5% | 40% | 30% |
| a fungicidal triazole (hexaconazole) | 20% | 2.5% | 8% | 1.5% |
| ethylene glycol | 10% | 10% | 10% | 10% |
| nonylphenol polyethylene glycol ether (15 moles of ethylene oxide) | 6% | 1% | 5% | 7.5% |
| sodium lignosulfate | 10% | 5% | 9% | 11% |
| carboxymethylcellulose | 1% | 1% | 1% | 1% |
| 37% aqueous formaldehyde solution | 0.2% | 0.2% | 0.2% | 0.2% |
| silicone oil in the form of a 75% aqueous emulsion | 0.8% | 0.8% | 0.8% | 0.8% |
| water | 32% | 77% | 26% | 38% |

The active ingredients were intimately mixed with the adjuvants, giving a suspension concentrate from which suspension of any desired concentration could be obtained by dilution with water.

| | e) | f) | g) |
|---|---|---|---|
| metconazole | 5% | 2.5% | 10% |
| a fungicidal triazole (penconazole) | 5% | 2.5% | 5% |
| polyethylene glycol (MG 400) | 70% | — | — |
| N-methyl-2-pyrrolidone | 20% | — | — |
| epoxidised coconut oil | — | 1% | 1% |
| petroleum distillate (boiling range 160–190° C.) | — | 94% | 84% |

These solutions were suitable for application in the form of microdrops.

B) COMPOSITION EXAMPLES (Wood protection)

| Example 7: Water-dilutable concentrates | a) | b) | c) | d) |
|---|---|---|---|---|
| metconazole | 3 | 2 | 1 | 0.5 |
| triazole (propiconazole) | 1 | 2 | 3 | 3.5 |
| $CU(OH)_2CuCO_3$ | 14 | 14 | 14 | 14 |
| monoethanolamine | 33.5 | 33.5 | 33.5 | 27 |
| water | 19 | 10.5 | 10.5 | 10.5 |
| nonylphenol polyethylene glycol ether (10 moles of ethylene oxide) | 10 | 10 | 10 | 10 |
| propylene glycol | 6 | 6 | 6 | 6 |
| boric acid | 7.5 | — | — | — |
| propionic acid | 6 | — | — | — |

-continued

| Example 7: Water-dilutable concentrates | a) | b) | c) | d) |
|---|---|---|---|---|
| benzoic acid | — | 22 | 22 | 21 |
| polymin (n = 150) | — | — | — | 7.5 |

C. BIOLOGICAL EXAMPLES

Example 8

The synergistic activity of the mixtures or compositions of (I) and (II) according to the present invention can be demonstrated by comparison with the activity of the active ingredients (I) and (II) alone. The efficacy of the active ingredients against mycelial growth and sporulation of *Coriolus versicolor, Gloeophyllum trabeum, Coniophora puteana, Poria monticola, Coriolus versicolor* and *Lentinus edodus* was determined in the poison plate assay. The required concentrations of the fungicide(s) were obtained by diluting the active ingredients (I), (II) or the combination of (I) and (II) dissolved in 50% aqueous ethanol with a calculated amount of sterile water and pouring said dilutions in Petri-dishes. Malt extract agar (3%) was added aseptically and uniform distribution was obtained by shaking. Each plate was inoculated with mycelium from the margin of an actively growing colony. After incubation at 22° C. and 70% relative humidity for a period long enough to allow complete growth of controls, diameters of colonies were measured. Relative activities were calculated by taking the absence of fungal growth (diameter 0 mm) as 100%. From the activity of the active ingredients alone, the expected activities E were calculated by using the so-called formula of Colby: (Colby, S. R. Weeds 1967, 15: 20–22), $$E = X + Y - \frac{X \cdot Y}{100}$$

wherein X and Y express the relative activities obtained for each of the active ingredients. A synergistic effect can be acknowledged if the found activity exceeds calculated activity.

The results are listed in the table 1 below and clearly demonstrate that the measured activity generally exceeds the calculated activity. Equal efficacy was observed whenever complete inhibition of fungal growth occured by one of the active ingredients (I) or (II) alone.

TABLE 1

Activity of propiconazole, metconazole and their mixture against various basidiomycetes

| Propiconazole conc. (ppm) | Metconazole conc. (ppm) | Measured activity (%) | Calculated activity (%) |
|---|---|---|---|
| *Gloeophyllum trabeum* | | | |
| 10 | | 90 | |
| 5 | | 86 | |
| 2.5 | | 80 | |
| | 0.25 | 92 | |
| 10 | 0.25 | 100 | 99 |
| 5 | 0.25 | 100 | 99 |
| 2.5 | 0.25 | 100 | 98 |
| *Coniophora puteana* | | | |
| 1.25 | | 46 | |
| | 0.5 | 18 | |
| | 0.25 | 14 | |
| | 0.125 | 0 | |

TABLE 1-continued

Activity of propiconazole, metconazole and their mixture against various basidiomycetes

| Propiconazole conc. (ppm) | Metconazole conc. (ppm) | Measured activity (%) | Calculated activity (%) |
|---|---|---|---|
| 1.25 | 0.5 | 76 | 56 |
| 1.25 | 0.25 | 78 | 54 |
| 1.25 | 0.125 | 84 | 46 |
| *Poria monticola* | | | |
| 1.25 | | 72 | |
| | 0.25 | 28 | |
| | 0.125 | 8 | |
| 1.25 | 0.25 | 86 | 80 |
| 1.25 | 0.125 | 84 | 74 |
| *Coriolus versicolor* | | | |
| 2.5 | | 80 | |
| 1.25 | | 58 | |
| | 0.5 | 16 | |
| | 0.25 | 0 | |
| 2.5 | 0.5 | 100 | 83 |
| 2.5 | 0.25 | 100 | 80 |
| 1.25 | 0.5 | 100 | 65 |
| 1.25 | 0.25 | 100 | 58 |
| *Lentinus elodus* | | | |
| 5 | | 79 | |
| 2.5 | | 53 | |
| 1.25 | | 19 | |
| | 0.125 | 66 | |
| 5 | 0.125 | 100 | 93 |
| 2.5 | 0.125 | 100 | 84 |
| 1.25 | 0.125 | 100 | 72 |

Example 9

A greenhouse experiment demonstrating synergistic action of metconazole and propiconazole against the powdery mildew *Erysiphe graminis* on wheat and barley.

MATERIAL AND METHODS

Test compounds were micronised by milling them for 10 minutes in a "Pulverisette 5" ball mill (Fritsch GMBH) and subsequently suspended in distilled water containing 0.05% macrogol as a dispersant. Treatment was performed as follows: two week old wheat or barley plants grown in 8 cm diameter plastic pots in garden soil were sprayed until runoff with suitable doses of the test compounds. Four hours later the treated plants were dusted with *Erysiphe graminis* conidia from infected wheat or barley plants respectively, and placed in the greenhouse. After one week the severity of the infection was estimated visually and expressed as % fungal attack as compared to untreated controls (100% fungal attack).

Synergy was determined by comparing observed % fungal attack values with expected values, calculated according to Limpel's formula, often called Colby's formula (Richer, 1987; Colby, 1967; Limpel et al., 1962).

Limpel's formula:

$$E = \frac{A \cdot B}{100}$$

Where
E=the expected % fungal attack when product 1 at dose a is combined with product 2 at dose b, supposing that the combined effect of both products is purely additive,
A=the % fungal attack observed when product 1 is applied alone at dose a, and B=the % fungal attack observed when product 2 is applied alone at dose b.

When the % fungal attack observed for a combination of compounds is appreciably lower than the expected value, synergy is assumed.

RESULTS

The results for *Erysiphe graminis* on wheat, expressed as % fungal attack, can be found in Table 2. Expected fungal attack values for each combination are added between brackets.

TABLE 2

% *Erysiphe graminis* attack on wheat plants treated with different combinations of propiconazole and metconazole. Each value is the mean of six replicates.

|  |  | propiconazole (ppm) | | | |
| --- | --- | --- | --- | --- | --- |
|  |  | 1 | 0,5 | 0,25 | 0 |
| metconazole (ppm) | 1 | 6 (79) | 8 (88) | 12 (88) | 88 |
|  | 0,5 | 20 (90) | 58 (100) | 100 (100) | 100 |
|  | 0,25 | 27 (90) | 80 (100) | 100 (100) | 100 |
|  | 0 | 90 | 100 | 100 | 100 |

As can be seen in table 2, synergy occurred with the following propiconazole: metconazole ratios: 1:1, 1:2, 1:4, 2:1 and 4:1.

The results for *Erysiphe graminis* on barley can be found in Table 3. Again, expected fungal attack values for each combination are added between brackets.

TABLE 3

*Erysiphe graminis* attack on barley plants treated with different combinations of propiconazole and metconazole. Each value is the mean of six replicates.

|  |  | propiconazole (ppm) | | | |
| --- | --- | --- | --- | --- | --- |
|  |  | 8 | 4 | 2 | 0 |
| metconazole (ppm) | 2 | 7 (30) | 38 (100) | 100 (100) | 100 |
|  | 1 | 100 (100) | 100 (100) | 100 (100) | 100 |
|  | 0,5 | 100 (100) | 100 (100) | 100 (100) | 100 |
|  | 0 | 30 | 100 | 100 | 100 |

As can be seen in Table 3, synergy occurred with 2:1 and 4:1 propiconazole:metconazole ratios.

REFERENCES

Colby, S. R. (1967) *Weeds* 15: 20–22
Limpel, L. E. et al (1962) *Proc. N. E. Weed Control Conf.* 16: 48–53
Richer, D. L. (1987) *Pestic. Sci.* 19: 309–315

We claim:

1. A fungicidal composition comprising synergistic fungicidally effective amount of (I) metconazole, a salt, a stereoisomer or a stereoisomeric mixture thereof, and (II) cyproconazole, a salt, a stereoisomer or a stereoisomeric mixture thereof and a carrier and wherein the proportion of (I) to (II) is within the range of from 50:1 to 1:50, by weight.

2. A plant protection composition comprising the composition of claim 1 further comprising a cationic surfactant.

3. A material protection composition comprising the composition of claim 1 further comprising a copper compound.

4. A composition according to claim 3 further comprising a non-ionic surfactant.

5. A method of combating fungi comprising treating plants or the loci thereof simultaneously, separately or sequentially with an effective amount of a synergistic, fungicidal composition as defined in claim 1.

6. A method of combating fungi comprising treating plants or the loci thereof simultaneously, separately or sequentially with an effective amount of a synergistic, fungicidal composition as defined in claim 2.

7. A method of combating fungi comprising treating wood simultaneously, separately or sequentially with an effective amount of a synergistic, fungicidal composition as defined in claim 1.

8. A method of combating fungi comprising treating pulpwood for paper manufacture simultaneously, separately or sequentially with an effective amount of a synergistic, fungicidal composition as defined in claim 1.

9. A method of combating fungi comprising treating biodegradable materials simultaneously, separately or sequentially with an effective amount of a synergistic, fungicidal composition as defined in claim 1.

10. A method of combating fungi comprising treating biodegradable materials simultaneously, separately or sequentially with an effective amount of a synergistic, fungicidal composition as defined in claim 3.

11. A method of combating fungi comprising treating biodegradable materials simultaneously, separately or sequentially with an effective amount of a synergistic, fungicidal composition as defined in claim 4.

12. A method of preserving wood, wood products and biodegradable materials, characterized by treating the wood, wood products and biodegradable materials with an effective amount of a synergistic, fungicidal composition as defined in claim 1.

13. A method of preserving wood, wood products and biodegradable materials, characterized by treating the wood, wood products and biodegradable materials with an effective amount of a synergistic, fungicidal composition as defined in claim 3.

14. A method of preserving wood, wood products and biodegradable materials, characterized by treating the wood, wood products and biodegradable materials with an effective amount of a synergistic, fungicidal composition as defined in claim 4.

* * * * *